United States Patent [19]

Cain et al.

[11] 4,198,987
[45] Apr. 22, 1980

[54] MEASURING SYSTEM INCLUDING ELEMENTS IMPLANTABLE BENEATH THE SKIN

[76] Inventors: Clarence P. Cain, 2870 Ludlow Rd., Cleveland, Ohio 44120; David D. Michie, 1377 Wainwright Way, Ft. Myers, Fla. 33907

[21] Appl. No.: 867,891

[22] Filed: Jan. 9, 1978

[51] Int. Cl.² ............................................. A61B 5/02
[52] U.S. Cl. ................................................... 128/663
[58] Field of Search .................. 128/2 P, 2 R, 2.05 E, 128/2.05 F, 2.05 R, 2.1 A, 2.1 P, 419 PG, 419 PS, 419 PT, 419 R, 630, 631, 660–663, 668, 903, 908

[56] References Cited

U.S. PATENT DOCUMENTS

| | | | |
|---|---|---|---|
| 3,430,625 | 3/1969 | McLeod, Jr. | 128/2.05 F |
| 3,672,352 | 6/1972 | Summers | 128/2.1 A |
| 4,041,954 | 8/1977 | Ohara | 128/2.1 A |

*Primary Examiner*—William E. Kamm
*Attorney, Agent, or Firm*—V. Lawrence Sewell

[57] ABSTRACT

A system is disclosed having a portion permanently implantable beneath the skin to perform in vivo measurements, such as Doppler ultrasonic blood flow velocity measurements. Measurement information is transmitted out through the skin by means of ultrasonic vibrations radiated by one piezoelectric crystal and received by another. Power is transferred into the implanted portion of the system at an audio frequency by inducing current in an implanted coil.

3 Claims, 2 Drawing Figures

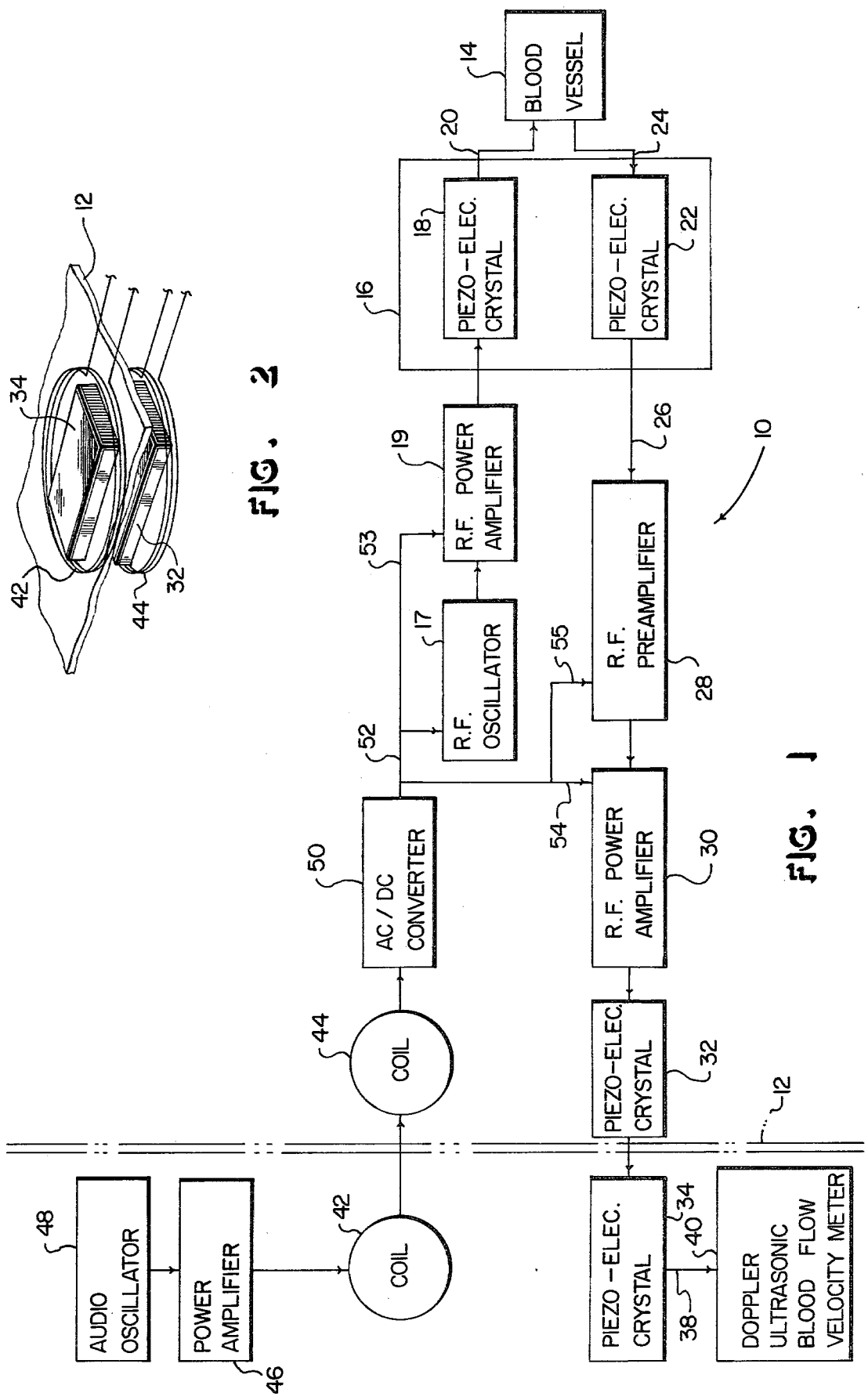

MEASURING SYSTEM INCLUDING ELEMENTS IMPLANTABLE BENEATH THE SKIN

BACKGROUND OF THE INVENTION

This invention relates to an implantable system for use in the performance of in vivo measurements beneath the skin. More particularly, there is included a system for performing measurements of blood flow velocity.

There are a number of reasons for implanting instrumentation in the body. It may be that the instrumentation is to be active over an extended period, either continuously or repeated from time to time. It may be considerably more desirable to activate the instrumentation, such as a measurement system, during more or less normal activity, rather than being restricted to using the instrumentation in the body in a surgical environment.

There are also a number of problems associated with implaning instrumentation. Many of these have to do with the inviolability of the skin. It is most desirable that the skin completely heal over an implantation insertion and that no wires or other devices pass through the skin, requiring openings in its protective barrier of the body. As a result, there are abiding problems of supplying power from the outside into the implanted instrumentation and of transmitting information through the skin, usually from beneath the skin to the outside.

SUMMARY OF THE INVENTION

In accordance with the present invention, there is provided a system for use in the performance of measurements beneath the skin. This system includes transmission means beneath the skin for wirelessly transmitting signals out through the skin. Conditioning means, also beneath the skin, can be connected to a subcutaneous transducer to provide the transmission means with signals which are suitable for transmission and which contain the information from the transducer. A reception means on the outside of the skin receives the transmitted signals and makes the information from the transducer available outside.

Further in accordance with the invention, there is provided an entire measurement system using an implantable Doppler ultrasonic blood flow velocity measuring probe or transducer. The system includes means for amplifying the output of the probe to drive a piezoelectric crystal implanted just beneath the skin. The crystal radiates ultrasonic vibrations, containing velocity information from the probe, through the skin. Outside the skin, another piezoelectric crystal receives the vibrations and generates an electrical signal output capable of being processed by a conventional Doppler ultrasonic blood flow velocity meter. Power is supplied to the implanted portion of the system by applying an audio frequency current to a coil outside the skin and inducing a current in a similar coil implanted just beneath the skin.

The system of the invention has no wires or other elements penetrating the skin and constituting possible sites of infection. The system does not depend on batteries; therefore, it can be operated for an indefinitely long period. After the initial implantation, there is no need to reopen the skin. Measurements can be repeatedly made over an extended period and under a variety of conditions.

The system of the invention can be used, particularly in the body of an experimental animal, to evaluate exercise, pharmacologic agents, surgical procedures, disease states and other interventions upon blood flow. Clinically, the system could be used to evaluate blood flow velocities following vascular or cardiovascular surgical procedures, avoiding the inherent dangers associated with methods which require injecting a foreign material such as a radio-opaque substance into the vascular system.

These and other features and advantages will become apparent from a consideration of the description of the preferred embodiment which follows.

BRIEF DESCRIPTION OF THE DRAWING

FIG. 1 is a system block diagram of a Doppler ultrasonic blood flow velocity measuring system according to the invention.

FIG. 2 is a partially schematic perspective view of the physical placement, with respect to the skin, of elements in the system of FIG. 1.

DESCRIPTION OF PREFERRED EMBODIMENTS

FIG. 1 is a block diagram of a blood flow velocity measuring system embodying the principles of the invention. The measuring system is indicated generally by the reference numeral 10. The portion of system 10 to the right of line 12 is implanted beneath the skin; the elements to the left of line 12 are outside the body. A blood vessel in which the flow velocity is to be measured is indicated by a numeral 14.

An ultrasonic blood flow velocity measuring probe or transducer 16 is coupled to blood vessel 14. The flow probe can be of a commercially available type, such as that marketed by Parks Electronics, which has two parts that are fitted together, forming a sleeve, around a blood vessel. The probe includes a piezoelectric crystal 18 which is driven to radiate the blood vessel 14 with ultrasound, as indicated by input 20. Radio frequency oscillator 17 generates oscillations at a frequency for which the probe 16 is designed, for example 10 MHZ. These oscillations are applied to radio frequency power amplifier 19 which, in turn, provides the drive for crystal 18.

Some of the ultrasonic energy from crystal 18 is reflected and impinges (input 24) on a second piezoelectric crystal 22 in probe 16. Crystal 22 provides a radio frequency electrical signal output 26 which is analogous (proportional) to the impinging ultrasound vibrations and which contains information as to the velocity of blood flow in vessel 14.

As the ultrasonic vibrations are reflected from the flowing blood, the frequency of the vibrations is altered, according to the Doppler effect, by an amount dependent on the flow velocity. Thus, the information as to the instantaneous flow velocity is contained in the reflected vibrations as a modulation of the waveform radiated by crystal 18, which may be regarded as a carrier waveform.

Radio frequency preamplifier 28 and power amplifier 30 serve to amplify the output 26 of crystal 22 sufficiently to drive a third piezoelectric crystal 32. Crystal 32 and a fourth piezoelectric crystal 34 are shown in both FIGS. 1 and 2. FIG. 2 is a semi-schematic drawing illustrating the physical placement of some elements of system 10. Piezoelectric crystal 32 is implanted just beneath the skin 12, while crystal 34 is placed against the outside of the skin, opposite crystal 32. Crystal 32 is driven by the amplified radio frequency output of amplifier 30 to radiate ultrasonic vibrations through the skin to the outside. Crystal 34, operating in the same manner as crystal 22, receives the vibrations on the outside of the skin and generates an electrical signal output 38.

Crystal 22, amplifiers 28 and 30 and crystals 32 and 34 are all substantially linear devices, the output of each device being proportional to its input. As a result, the waveform of output 38 of crystal 34 is the same waveform as output 26 of crystal 22, within the limits of the accuracy of the linear devices involved. If the blood flow velocity measurements were being made through an opening in the skin, output 26 would be directly connected to a Doppler ultrasonic blood fow velocity meter which would determine the flow velocity thereform. In system 10, such a velocity meter 40 is connected to signal output 38 to interpret the frequency shifts in the waveform and determine the flow velocity in blood vessel 14. The meter can be, for example, a commercially available unit of Parks Electronics.

Power is provided to the implanted portion of system 10 by means of coils 42 and 44, illustrated both in FIGS. 1 and 2. In a preferred embodiment, coil 42 is packaged with crystal 34 and coil 44 is packaged with crystal 32. Coil 42 is connectable to a power source comprised of power amplifier 46 driven by audio oscillator 48. There is sufficient inductive coupling between coils 42 and 44, that an audio frequency current in coil 42 induces a current flow in coil 44. The frequency of the currents in the coils is set by audio oscillator 48 to be high enough to provide good inductive coupling between the coils, but not so high as to be extremely attenuated by the skin tissue separating the coils. Audio oscillator 48 can be set, for example, to 11 kilohertz.

The current and voltage induced in coil 44 are converted to direct current form by AC/DC converter 50 and supplied to other elements of the implanted portion of system 10 as indicated by paths 52-55. Included among the elements supplied by converter 50 are oscillator 17, power amplifier 19, preamplifier 28 and power amplifier 30.

The implanted portion of system 10 is miniaturized and occupies only a small space below the skin, despite its relatively large number of elements. As is well known in the art, the implanted portion must be enclosed in a covering which will protect it from the environment of the body and minimize reaction of the body to the implantation.

In the use of system 10, the portion to the right of line 12 in FIG. 1 is implanted in a human patient or experimental animal object, with crystal 32 and coil 44 placed just beneath the skin. The implanting incision is closed and allowed to heal. When measurements are to be made, crystal 34 and coil 42 are placed against the skin above crystal 32 and coil 44. Meter 40 is connected to output 38 of crystal 34 to determine blood flow velocity. Oscillator 48 and amplifier 46 are connected to provide power to coil 44.

After the implantation, the use of measurement system 10 becomes a straightforward, low risk, non-invasive technique. No new incisions need be made in order to make accurate blood flow determinations. Nor are there elements penetrating the skin which could allow infection. The performance of the measurements can be continued over an indefinitely long period, since power is supplied via coils 42 and 44 rather than by batteries implanted with the system.

The system 10 offers certain economies. Not only can the transducer 16 be a commercially available probe, but the output 38 of crystal 34 is ordinarily substantially the same as that of the probe. As a result, output 38 can be accepted as an input by the blood flow meter which is sold to accept the input of transducer 16.

There are features of measuring system 10 which may be employed to advantage in other implanted systems. Transducers of mechanical vibrations, such as piezoelectric crystals 32 and 34 can be employed to transfer information other than blood flow information through the skin. In the system 10, the output of the transducer or probe 16 happens to be coded in a form that is capable of transmission by the crystals 32 and 34. The only conditioning means required between the transducer and the crystal 32 are the radio frequency preamplifier 28 and amplifier 30. In other cases, the output of the implanted transducer could be in a form not immediately suitable for transmission, such as a voltage analog of blood pressure. In these cases, conditioning means could include a radio frequency carrier oscillator and a frequency or amplitude modulation circuit. The radio frequency carrier would be modulated by the transducer output and the resulting waveform used to drive the piezoelectric crystal beneath the skin. The output of the external crystal would be connected to a demodulation circuit to derive the transducer waveform.

For some transducers, the carrier used to transmit information across the skin would not need to be at a radio frequency. If the frequencies contained in the transducer output were sufficiently low, an audio frequency carrier would suffice. Here, a conventional audio frequency driver capable of implantation could be used instead of a piezoelectric crystal. The audio frequency mechanical vibrations would have the advantage of lower attenuation in the skin than the ultrasound.

Piezoelectric crystals such as crystals 32 and 34 may also be used to transmit information into the body to an implanted system. In this case, a modulated radio frequency signal could be applied to the external crystal which would transmit the information by means of ultrasonic vibrations through the skin to the implanted crystal. The implanted portion of the system would include a demodulation circuit to obtain the information for use inside the body.

Although preferred embodiments of the invention have been described in detail, it is to be understood by various changes, substitutions and alterations can be made therein without departing from the spirit and scope of the invention as defined by the appended claims.

What I claim is:

1. A system for performing blood flow measurements beneath the skin, comprising:
   means, on the outside of the skin, including a first coil connectable to a power source for transmitting power through the skin at an audio frequency;
   elements to be located beneath the skin, comprising:
      means, including an oscillator and amplifier, for generating electrical oscillations of a selected radio frequency,
      an ultrasonic blood flow probe comprised of
         means, including a first piezoelectric crystal, driven by said oscillations, for radiating a blood vessel with ultrasonic vibrations at said frequency and means, including a second piezoelectric crystal for receiving ultrasonic vibrations reflected from blood flowing in said vessel and providing an electrical signal output, analogous to the received reflected vibrations and containing information of the velocity of the blood flow, means for amplifying said electrical signal output, means, including a third piezoelectric crystal for radiating ultrasonic vibrations, analogous to said amplified electrical signal output, through the skin to the outside, means, including a second coil near said first coil, for receiving said audio frequency power by electromagnetic induction, and means for converting the received power to a direct current form and supplying said elements beneath the skin therewith; and reception means on the outside of the skin, including a fourth piezoelectric crystal, for receiving said ultrasonic vibrations radiated to the outside and providing an external electrical signal output analogous to the outside vibrations, whereby said external output is analogous to said received vibrations reflected from the blood in said vessel.

2. The system of claim 1, further including means for determining, from the external output, said blood flow velocity.

3. A system for performing blood flow measurements beneath the skin, comprising:

elements to be located beneath the skin, comprising means, including an oscillator and amplifier, for generating electrical oscillations of a selected radio frequency, an ultrasonic blood flow probe comprised of means, including a first piezoelectric crystal, driven by said oscillations, for radiating a blood vessel with ultrasonic vibrations at said frequency and means, including a second piezoelectric crystal for receiving ultrasonic vibrations reflected from blood flowing in said vessel and providing an electrical signal output, analogous to the received reflected vibrations and containing information of the velocity of the blood flow, means for amplifying said electrical signal output, means, including a third piezoelectric crystal for radiating ultrasonic vibrations, analogous to said amplified electrical signal output, through the skin to the outside; and reception means on the outside of the skin, including a fourth piezoelectric crystal, for receiving said ultrasonic vibrations radiated to the outside and providing an external electrical signal output analogous to the outside vibrations, whereby said external output contains said blood flow velocity information.

* * * * *